United States Patent [19]

Muijs et al.

[11] Patent Number: 4,693,311
[45] Date of Patent: Sep. 15, 1987

[54] STEAM FOAM PROCESS

[75] Inventors: Herman M. Muijs; Paulus P. M. Keijzer, both of Rijswijk, Netherlands

[73] Assignee: Shell Internationale Maatschappij, B.V., Netherlands

[21] Appl. No.: 875,412

[22] Filed: Jun. 17, 1986

[30] Foreign Application Priority Data

Jul. 4, 1985 [GB] United Kingdom ................ 8516920

[51] Int. Cl.⁴ .............................................. E21B 43/24
[52] U.S. Cl. ...................................... 166/272; 166/273
[58] Field of Search ............... 166/303, 309, 272, 273, 166/275

[56] References Cited

U.S. PATENT DOCUMENTS

| 3,318,379 | 3/1967 | Bond et al. | 166/273 |
| 3,330,346 | 7/1967 | Jacobs et al. | 166/273 |
| 4,086,964 | 5/1978 | Dilgren et al. | 166/27 L |
| 4,191,252 | 3/1980 | Buckley et al. | 166/303 X |
| 4,364,431 | 12/1982 | Suidi et al. | 166/275 |
| 4,570,711 | 2/1986 | Falls et al. | 166/303 X |
| 4,579,176 | 4/1986 | Davies et al. | 166/303 |

*Primary Examiner*—Stephen J. Novosad
*Assistant Examiner*—Thomas J. Odar
*Attorney, Agent, or Firm*—Jones, Tullar & Cooper

[57] ABSTRACT

A steam foam process for diverting steam within a subterranean reservoir and improving oil displacement is carried out by injecting into the reservoir a steam-foam-forming mixture comprising steam and a linear $C_{25}$–$C_{30}$-α-olefin sulphonate surfactant, and preferably a non-condensable gas.

12 Claims, 2 Drawing Figures

STEAM FOAM PROCESS

The invention relates to a steam foam process for producing oil from, or displacing oil within, a subterranean reservoir.

In certain respects, this invention is an improvement in the steam-channel-expanding steam foam drive process described in U.S. Pat. No. 4,086,964 (issued on May 2, 1978 to R. E. Dilgren, G. J. Hirasaki, H. J. Hill and D. G. Whitten.

The invention is particularly useful in an oil producing process of the type described in the above noted patent.

In this process steam is injected into, and fluid is produced from, horizontally spaced locations within a portion of an oil reservoir in which the disposition of a steam flow path is determined by gravity and/or oil distribution. After a steam channel has been formed the composition of the fluid being injected is changed from steam to a steam-foam-forming mixture. The composition of the mixture is correlated with the properties of the rocks and the fluids in the reservoir so that the pressure required to inject the mixture and to move it through the steam channel exceeds that required for steam alone but is less than the reservoir fracturing pressure. The composition and rate of injecting the mixture is subsequently adjusted to the extent required to maintain a flow of steam foam within the channel at a relatively high pressure gradient at which the oil-displacing and channel-expanding effects are significantly greater than those provided by the steam alone. Oil is recovered from the fluid produced from the reservoir.

The present invention also relates to an oil recovery process in which steam is cyclically injected into and fluid is backflowed from a heavy oil reservoir which is susceptible to a gravity override that causes an oil layer to become adjacent to a gas or vapour-containing substantially oil-desaturated zone in which there is an undesirable intake and retention of the injected fluid within the desaturated zone. In such a process, the steam to be injected is premixed with surfactant components arranged to form a steam foam within the reservoir having physical and chemical properties such that it (a) is capable of being injected into the reservoir without plugging any portion of the reservoir at a pressure which exceeds that required for injecting steam but is less than the reservoir fracturing pressure and (b) is chemically weakened by contact with the reservoir oil so that it is more mobile in sand containing that oil than in sand which is substantially free of that oil. The surfactant-containing steam is injected into the reservoir at a rate slow enough to be conducive to displacing a front of the steam foam along the oil-containing edge portions of the oil-desaturated zone than along the central portion of that zone. And, fluid is backflowed from the reservoir at a time at which part or all of the steam is condensed within the steam foam in the reservoir.

As used herein the following terms have the following meanings: "steam foam" refers to a foam i.e. gas-liquid dispersion which (a) is capable of both reducing the effective mobility, or ease with which such a foam or dispersion will flow within a permeable porous medium and (b) has steam in the gas phase thereof. "Mobility" or "permeability" refers to an effective mobility or ease of flow of a foam within a permeable porous medium. A "permeability reduction" or "mobility reduction" refers to reducing the ease of such a foam flow due to an increase in the effective viscosity of the fluid and/or a decrease in the effective permeability of the porous medium. A reduction in such a mobility or permeability can be detected and/or determined by measuring differences in internal pressures within a column of permeable porous material during a steady state flow of fluid through a column of such material. "Steam quality" as used regarding any steam-containing fluid refers to the weight percent of the water in that fluid which is in the vapour phase of the fluid at the boiling temperature of that water at the pressure of the fluid. For example: in a monocomponent steam-containing fluid which consists entirely of water and has a steam quality of 50%, one-half of the weight of the water is in the vapour phase; and, in a multicomponent steam-containing fluid which contains nitrogen in the vapour phase and dissolved or dispersed surfactant and electrolyte in the liquid phase and has a steam quality of 50%, one-half the weight of the weight of the water in the multicomponent steam-containing fluid is in the vapour phase. Thus, the steam quality of a steam-containing fluid can be calculated as, for example, 100 times the mass (or mass flow rate) of the water vapour in that fluid divided by the sum of the mass (or mass flow rate) of both the water vapour and the liquid water in that fluid. "Steam-foam-forming mixture" (or composition) refers to a mixture of steam and aqueous liquid solution (or dispersion) of surfactant, with some or all, of the steam being present in the gas phase of a steam foam. The gas phase may include noncondensable gas(es) such as nitrogen.

An object of the invention is an improved process for displacing oil within an oil-containing subterranean reservoir by flowing a steam-containing fluid in conjunction with a surfactant component through a relatively steam permeable zone within the reservoir.

According to the invention the surfactant component comprises in substantial part at least one linear $C_{25}$–$C_{30}$-α-olefin sulphonate.

The linear $C_{25}$–$C_{30}$-α-olefin sulphonate-containing steam-foam-forming mixture suitably includes an aqueous solution of electrolyte and advantageously further also includes a substantially noncondensable gas; with each of the surfactant, electrolyte and gas components being present in proportions effective for steam-foam-formation in the presence of the reservoir oil. The invention also relates to the linear $C_{25}$–$C_{30}$-α-olefin sulphonate-containing steam-foam-forming mixtures which are described herein.

The invention is useful where it is desirable to remove oil from, or displace oil within, a subterranean reservoir. For example, the invention can be used to move oil or an emulsion of oil and water away from a well borehole in a well-cleaning type of operation, and/or to displace oil into a producing location in an oil-recovery operation.

In particular, the present invention relates to a process for recovering oil from a subterranean reservoir, comprising:

injecting steam and producing fluid at horizontally spaced locations within a portion of an oil reservoir in which the disposition of a steam flow path is determined by the effect of gravity and/or oil distribution, rather than being substantially confined within at least the one most permeable layer of reservoir rocks;

advantageously maintaining rates of steam injecting and fluid production such that a steam channel has been extended from the injection location;

changing the composition of the fluid being injected from steam to a steam-foam-forming mixture including steam and an aqueous, electrolyte-containing solution or dispersion of a linear-$C_{25}$-$C_{30}$-$\alpha$-olefin sulphonate-containing surfactant, whilst continuing to produce fluid from the reservoir;

correlating the composition of the steam-foam-forming mixture with the properties of the rocks and fluids in the reservoir so that the pressure required to inject the mixture and the foam it forms or comprises into and through the steam channel exceeds that required for steam alone but is less than the reservoir fracturing pressure; and adjusting the composition of the fluid being injected into the steam channel to the extent required to maintain a flow of both steam and foam within the channel in response to a relatively high pressure gradient at which the oil-displacing and channel expanding effects are significantly greater than those provided by steam alone, without plugging the channel.

The invention also relates to an oil recovery process in which steam is cyclically injected into and fluid is backflowed from a subterranean heavy oil reservoir which is susceptible to gravity override and tends to intake and retain undesirably large proportions of the injected fluid. This process comprises:

(1) injecting steam mixed with a linear $C_{25}$-$C_{30}$-$\alpha$-olefin sulphonate-containing steam-foam-forming compound which is arranged for forming a steam foam which (a) can be displaced through the pores of the reservoir, without plugging any portion of the reservoir, in response to a pressure which exceeds that required for displacing steam through the reservoir but is less than the fracturing pressure of the reservoir, and (b) can be weakened by contact with the reservoir oil to an extent such that the weakened foam is significantly more mobile in reservoir oil-containing pores of a porous medium than in oil-free pores of that medium;

(2) injecting the steam-foam-forming mixture at a rate equivalent to one which is slow enough to cause the foam formed by that mixture to advance more rapidly through the pores of a reservoir oil-containing permeable medium than through the pores of a substantially oil-free permeable medium; and (3) backflowing fluid from the reservoir after a steam soak time sufficient to condense part or all of the steam in the injected steam-foam-forming mixture. The steam-foam-forming mixture preferably comprises steam, a noncondensable gas, a linear $C_{25}$-$C_{30}$-$\alpha$-olefin sulphonate surfactant and an electrolyte.

The invention provides unobvious and beneficial advantages in oil displacement procedures by the use of the linear-$C_{25}$-$C_{30}$-$\alpha$-olefin sulphonate surfactant in the steam-foam-forming compositions. For example, where a steam-foam-forming mixture contains such a surfactant and an electrolyte in proportions near optimum for foam formation, the present surfactant components provide exceptionally strong steam foams having mobilities many times less than those of steam foams using other surfactants. In addition, significant reductions are reached in the mobilities of the steam foams at concentrations which are much less than those required for equal mobility reductions by the surfactants which were previously considered to be the best available for such a purpose. The use of the present linear $C_{25}$-$C_{30}$-$\alpha$-olefin sulphonate surfactant components involves no problems with respect to thermal and hydrolytic stability. No chemical or physical deterioration has been detectable in the present linear $C_{25}$-$C_{30}$-$\alpha$-olefin sulphonate surfactants that were recovered along with the fluids produced during productions of oil from subterranean reservoirs. In each of those types of sulphonate surfactants the sulphur atoms of the sulphonate groups are bonded directly to carbon atoms. The surfactants which were recovered and tested during the production of oil had travelled through the reservoirs at steam temperatures for significant times and distances.

The present linear $C_{25}$-$C_{30}$-$\alpha$-olefin sulphonate-containing steam foams have been found to represent a substantial improvement in mobility reduction over foams based on the alkylaryl sulphonates e.g., dodecylbenzene sulphonates. The foams to be used according to the present invention represent also substantial improvement over the $C_{16}$-$C_{24}$ alpha-olefinsulphonate-containing foams.

The present invention further relates to compositions containing at least one linear $C_{25}$-$C_{30}$-$\alpha$-olefin sulphonate, and steam, optionally electrolyte, and optionally noncondensable gas, that are suitable for use in oil-displacing and/or producing processes. Of particular interest in this respect are steam-foam-forming compositions consisting essentially of (a) water, which is present in the composition, at a temperature substantially equalling its boiling temperature, at the pressure of the composition, in both a liquid phase and a vapour phase; (b) a surfactant component present in the liquid phase of the composition in an amount between 0.01 and 10 percent by weight, calculated on the weight of the liquid phase, said surfactant component comprising in substantial part at least one linear $C_{25}$-$C_{30}$-$\alpha$-olefin sulphonate; (c) an electrolyte present in the liquid phase of the composition in an amount between 0.001 percent by weight (calculated on the weight of the liquid phase) and an amount tending to partition the surfactant into a separate liquid phase; and (d) a noncondensable gas present in the vapour phase in an amount between about 0.0001 and 0.3 percent by mol, calculated on total mols in the vapour phase.

Illustrative of the linear $C_{25}$-$C_{30}$-$\alpha$-olefin sulphonate surfactants suitably employed in steam-foam drive processes of enhanced performance, according to the invention, are the sulphonates obtained by reacting a linear $C_{25}$-$C_{30}$-$\alpha$-olefin with sulphurtrioxide followed by neutralization of the sulphonic acid. Particularly suitable for purposes of the invention is a sulphonate derived from a substantially linear $C_{26}$-$C_{28}$-$\alpha$-olefin.

Different reservoir materials have different debilitating effects on the strength of a steam foam. Tests should therefore be carried out to determine the sulphonates or sulphonate-containing steam-foam-forming compositions that perform optimally in a given reservoir. This is preferably done by testing the influence of specific sulphonates on the mobility of a steam-containing fluid having the steam quality selected for use in the reservoir in the presence of the reservoir material.

Such tests are preferably conducted by flowing steam-containing fluids through a sand pack. The permeability of the sand pack and foam-debilitating properties of the oil in the sand pack should be at least substantially equivalent to those of the reservoir to be treated. Comparisons are made of the mobility of the steam-containing fluid with and without the surfactant component. The mobility is indicated by the substantially steady-state pressure drop between a pair of points located between the inlet and outlet portions of the sand pack in positions which are substantially free of end effects on the pressures.

Some laboratory tests to determine steam mobility will now be described with reference to FIGS. 1 and 2.

Figure 1:
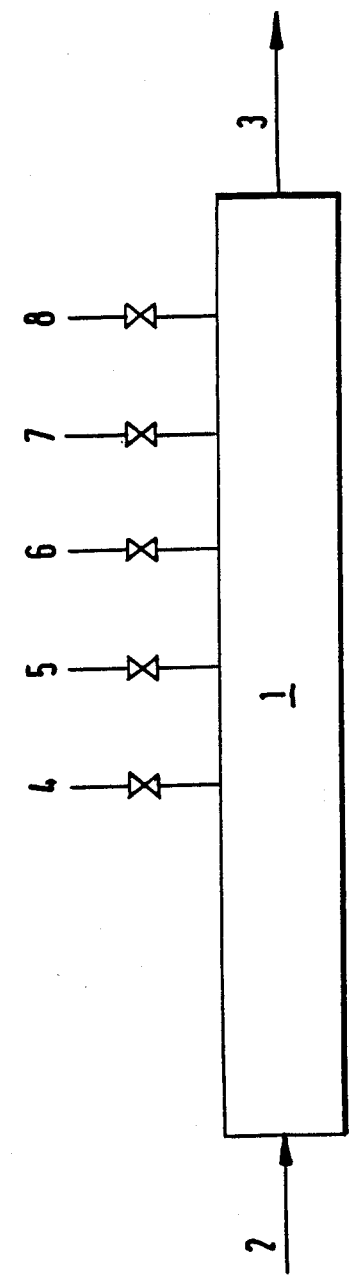
FIG. 1 shows schematically a sand pack test apparatus.

FIG. 1 shows schematically a sand pack test apparatus which can be made of currently available apparatus components. The apparatus consists of a cylindrical tube 1 that is b 400 mm long and has a cross-sectional area of 8 cm$^2$. Such a tube is preferably arranged for a horizontal flow of fluid from an inlet 2 to an outlet 3. The tube is preferably provided with 5 pressure taps 4, 5, 6, 7 and 8. The location of the first pressure tap 4 is at a distance of 150 mm from the inlet 2. The locations of the other taps are chosen so as to divide the part of the tube 1 situated behind tap 4 into equal parts of 50 mm. The tube 1 contains a permeable and porous column of suitable material, such as a sand pack, which is capable of providing an adequately realistic laboratory model of a subterranean reservoir.

At the inlet end 2, the sand pack or equivalent column of permeable material is arranged to receive separate streams of steam, noncondensable gas such as nitrogen, and one or more aqueous liquid solutions or dispersions containing a surfactant to be tested and/or a dissolved or dispersed electrolyte. Some or all of those components are injected at constant mass flow rates proportioned so that steam of a selected quality, or a selected steam-containing fluid or composition, or a steam-foam-forming mixture of a selected steam quality can be injected and will be substantially homogeneous as soon as it enters the face of the sand pack.

In the tests, steam-foam-forming mixtures are compared with and without surfactant components added thereto, by measuring pressure gradients formed within a sand pack during flows through the pack at the same substantially constant mass flow rate.

Numerous tests have been made of different steam-foam-forming mixtures using sand packs composed of a reservoir sand and having a high permeability, such as 10 darcys. The pressures were measured with pressure detectors (not shown) (such as piezoelectric devices) installed at the inlet 2 and at the taps 4, 5, 6, 7 and 8 of the tube 1. The results of such tests have proven to be generally comparable with the results obtained in the field.

In the laboratory tests, the steam-foam-forming components were injected at constant mass rates until substantially steady-state pressures were obtained at the inlet and at the taps. The ratio between the steady-state pressures at the taps during flow of steam mixed with the foam-forming surfactant component and the steady-state pressure at the taps during flow of the steam by itself are indicative for the mobility reduction. The higher this ratio, the stronger the steam foam and the higher the mobility reduction caused by the steam-foam-forming mixture.

Figure 2:
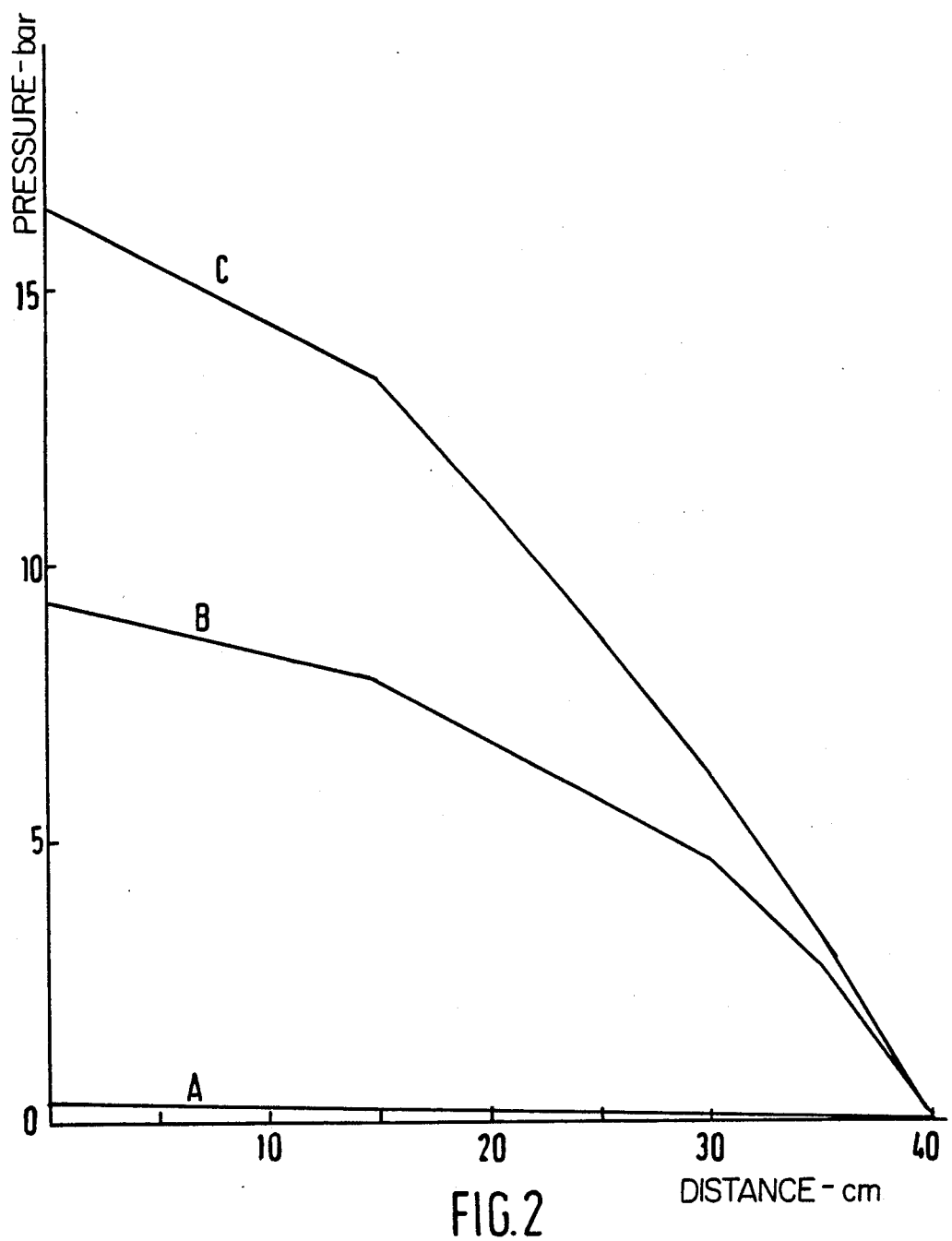
FIG. 2 illustrates the results of comparative tests with steam and various steam-foam-forming mixtures in sandpacks.

FIG. 2 illustrates the results of comparative tests with steam and various steam-foam-forming mixtures in sand packs containing Oude Pekela Reservoir sand having a permeability of 8 darcys. The backpressure was 21 bar, corresponding with a temperature of 215° C. The steam injection rate was 600 cm$^3$/min. The figure shows the variation of the pressure in bar (Y-axis) with distance in centimeters (X-axis) from the pack inlet 2. The pressures were measured at the inlet 2, at the taps 4, 5, 6, 7 and 8, and at the outlet 3 of the pipe 1 of FIG. 1. Curve A relates to the displacement wherein a mixture of 90% quality steam was used as a displacing composition.

Curve B relates to using a steam-containing fluid having a steam quality of 90% and a water phase which contains 0.5% by weight of a surfactant. In the Curve B test, the surfactant was a linear $C_{20}$-$\alpha$-olefin sodium sulphonate.

Curve C relates to using the mixture used for Curve B except that the surfactant was a linear $C_{26}$-$\alpha$-olefin sodium sulphonate.

The greatly improved steam permeability reduction performance of the presently described linear $C_{25}$–$C_{30}$-$\alpha$-olefin sulphonate-containing surfactant component is clear from the Curve C as compared to the Curves A and B in FIG. 2.

Compositions and procedures suitable for use in the present invention

For purposes of the present invention, the surfactant component of the steam-foam-forming mixture is necessarily comprised in substantial part of linear $C_{25}$–$C_{30}$-$\alpha$-olefin sulphonate. Materials of this class but with a much shorter alkyl chain have heretofore found commercial utility, for example, in detergent formulations for industrial, household and personal care application.

The class of sulphonates for use in the present invention is derived from a particular class of olefins, which may be defined for present purposes in terms of the configuration and number of carbon atoms in their molecular structure. These olefins have a carbon number from 25 to 30.

In terms of molecular structure, these olefins are aliphatic and linear. Alpha-olefins are considered suitable for the alkylation route chosen to produce the products to be used according to the invention. For purposes of derivation of the sulphonates for use in the process according to the invention, olefins are advantageously applied in which at least 90% of the molecules are alpha-olefins.

Particularly attractive are sulphonates derived from the Neodene alpha-olefins (trademark) sold by Shell Chemical Company, in part for their linear structure and high alpha-olefin content, i.e., greater than 95% in each case. The Neodene alpha-olefins are prepared by ethylene oligomerization.

The linear $C_{25}$–$C_{30}$-$\alpha$-olefins are reacted with sulphur trioxide. The term "sulphur trioxide" as used in the present specification and claims is intended to include any compounds or complexes which contain or yield $SO_3$ for a sulphonation reaction as well as $SO_3$ per se. This reaction may be conducted according to methods well known in the chemical arts, typically by contact of a flow of dilute $SO_3$ vapour with a thin film of liquid olefin at a temperature in the range of about 5° to 50° C. The reaction between the $SO_3$ and the olefin yields a sulphonic acid which is neutralized by reaction with a base, preferably an alkali metal hydroxide, oxide, or carbonate.

The specific composition of linear $C_{25}$–$C_{30}$-$\alpha$-olefin sulphonates prepared as described above (and also, for instance, the methods used for sulphonation, hydrolysis, and neutralization of the specified olefins) have not been found to be a critical factor to the performance of the surfactant in the steam foam process according to this invention. In this regard, it is observed that factors which have conventionally governed the choice of sulphonation conditions, e.g., product colour, clarity, odour, etc., do not carry the same weight in the preparation of linear $C_{25}$–$C_{30}$-α-olefin sulphonates for purposes of use in the process according to the invention that they have been accorded in detergent manufacture. Consequently, reaction conditions outside of those heretofore considered desirable for α-olefin sulphonation are still suitably applied in the preparation of surfactant components suitable for use in the steam-foam-forming mixture.

For purposes related to maintaining product stability, conventional manufacture typically yields a dilute solution or dispersion of the linear $C_{25}$–$C_{30}$-α-olefin sulphonates, for instance, products with a 15–30% wt active matter content in water. Such products may be directly applied to the preparation of steam-foam-forming mixtures for purposes of this invention.

Suitable linear $C_{25}$–$C_{30}$-α-olefin sulphonates, generally prepared by methods such as described above, are themselves commercially available products.

The strength of the foam formed by the steam-foam-forming composition including linear $C_{25}$–$C_{30}$-α-olefin sulphonate tends to increase with increases in the proportion of the surfactant and/or electrolyte components of the composition. Also, there tends to be an optimum ratio of surfactant and electrolyte components at which the surface activity of the composition is maximized.

The steam-foam-forming composition according to the present invention can form a steam-foam capable of reducing the effective mobility of the steam to less than about 1/10th and even to 1/50th-1/110th of the mobility it would have within a permeable porous medium in the absence of the surfactant.

The steam used in the present process and/or compositions can be generated and supplied in the form of substantially any dry, wet, superheated, or low grade steam in which the steam condensate and/or liquid components are compatible with, and do not inhibit, the foam-forming properties of the foam-forming components of a steam-foam-forming mixture according to the present invention. The steam quality of the steam as generated and/or amount of aqueous liquid with which it is mixed be such that the steam quality of the resulting mixture is preferably from 10 to 90%. The desired steamfoam is advantageously prepared by mixing the steam with aqueous solution(s) of the surfactant component and optionally, an electrolyte. The water content of these aqueous solutions must, of course, be taken into account in determining the steam quality of the mixture being formed.

Suitably, the noncondensable gas advantageously used in a steam-foam-forming mixture according to the present invention can comprise substantially any gas which (a) undergoes little or no condensation at the temperatures (100°–350° C.) and pressures (1–100 bar) at which the steam-foam-forming mixture is preferably injected into and displaced through the reservoir to be treated and (b) is substantially inert to and compatible with the foam-forming surfactant and other components of that mixture. Such a gas is preferably nitrogen but can comprise other substantially inert gases, such as air, ethane, methane, flue gas, fuel gas, or the like. Suitable concentrations of noncondensable gas in the steam-foam mixture fall in the range of from 0.0001 to 0.3 mole percent such as 0.001 and 0.2 mole percent, or between 0.003 and 0.1 mole percent of the gas phase of the mixture.

Suitably, the electrolyte used should have a composition similar to and should be used in a proportion similar to those described as suitable alkali metal salt electrolytes in previously noted U.S. Pat. No. 4,086,964. An aqueous solution may be applied that contains an amount of electrolyte substantially equivalent in salting-out effect to a sodium chloride concentration of from 0.001 to 10% (but less than enough to cause significant salting out) of the liquid-phase of the steam. Some or all of the electrolyte can comprise an inorganic salt, such as an alkali metal salt, an alkali metal halide, and sodium chloride. Other inorganic salts, for example, halides, sulphonates, carbonates, nitrates and phosphates, in the form of salts of alkaline earth metals, can be used.

Generally stated, an electrolyte concentration may be applied which has approximately the same effect on mobility reduction of the foam as does a sodium chloride concentration of between 0.001 and 5 percent by weight (but less than a salting out-inducing proportion) of the liquid phase of the steam-foam-forming mixture. The electrolyte concentration may be between 0.001 and 10 percent calculated on the same basis.

In compounding a steam-foam-forming mixture or composition in accordance with the present invention, the steam can be generated by means of substantially any of the commercially available devices and techniques for steam generation. A stream of the steam being injected into a reservoir is preferably generated and mixed, in substantially any surface or downhole location, with selected proportions of substantially non-condensable gas, aqueous electrolyte solution, and foam-forming surfactant. For example, in such a mixture, the quality of the steam which is generated and the concentration of the electrolyte and surfactant-containing aqueous liquid with which it is mixed are preferably arranged so that (1) the proportion of aqueous liquid mixed with the dry steam which is injected into the reservoir is sufficient to provide a steam-containing fluid having a steam quality of from 10–90% (preferably from 30–80%); (2) the weight proportion of surfactant dissolved or dispersed in the aqueous liquid is from 0.01 to 10.0 (preferably from 1.0 to 4.0); and (3) the amount of noncondensable gas is from 0.0003 to 0.3 mole fraction of the gas phase of the mixture.

We claim:

1. In a process for displacing oil within an oil-containing subterranean reservoir containing a relatively steam-permeable zone by flowing a steam-containing fluid in conjunction with a surfactant component through the relatively steam-permeable zone within said reservoir, the improvement wherein the surfactant component employed comprises in substantial part at light one linear $C_{25}$–$C_{30}$-α-olefin sulphonate.

2. A process according to claim 1, further wherein an electrolyte is employed in the flow within the reservoir in conjunction with the steam-containing fluid.

3. A process according to claim 1, further wherein a substantially non-condensable gas is employed in the flow within the reservoir in conjunction with the steam-containing fluid.

4. A process according to any one of claims 1, 2, 3 or 8, further wherein the surfactant comprises in substantial part sulphonate obtained by reacting a linear $C_{25}$–$C_{30}$-α-olefin with sulphur trioxide followed by neutralization of the sulfonic acid.

5. A process according to claim 4, further wherein the sulphonate is derived from linear $C_{26-28}$-α-olefin.

6. A process according to any one of claims 1, 2, 3 or 8, further wherein a steam-forming composition is formed and the aqueous liquid phase of the steam-foam-forming composition contains between 0.01 and 10 percent by weight of linear $C_{25}$–$C_{30}$-$\alpha$-olefin sulphonate.

7. A process according to one of claims 1, 2, 3 or 8, further wherein up to 10% of electrolyte is used in the liquid phase rather than nitrogen or another non-condensable gas to enhance the performance of the surfactant.

8. A process according to claim 2, further wherein a substantially non-condensable gas is employed in the flow within the reservoir in conjunction with the steam-containing fluid.

9. A process according to claim 4, further wherein a steam-foam-forming composition is formed and the aqueous liquid phase of the steam-foam-forming composition contains between about 0.001 and 10 percent by weight of linear $C_{25}$–$C_{30}$-$\alpha$-olefin sulphonate.

10. A process according to claim 4, further wherein up to 10% of electrolyte is used in the liquid phase rather than a nitrogen or another non-condensable gas to enhance the performance of the surfactant.

11. A process according to anyone of claims 1, 2, 3, or 8, further wherein up to 10% of electrolyte is used in the liquid phase in addition to nitrogen or another non-condensable gas to enhance the performance of the surfactant.

12. A process according to claim 4, further wherein up to 10% of electrolyte is used in the liquid phase in addition to nitrogen or another non-condensable gas to enhance the performance of the surfactant.

* * * * *

UNITED STATES PATENT AND TRADEMARK OFFICE
CERTIFICATE OF CORRECTION

PATENT NO. : 4,693,311

DATED : September 15, 1987

INVENTOR(S) : HERMAN M. MUIJS and PAULUS P.M. KEIJZER

It is certified that error appears in the above-identified patent and that said Letters Patent is hereby corrected as shown below: On the title page The Assignee's name should be

-- SHELL INTERNATIONALE RESEARCH MAATSCHAPPIJ B.V. --

Signed and Sealed this

Twenty-second Day of November, 1988

Attest:

DONALD J. QUIGG

Attesting Officer

Commissioner of Patents and Trademarks

UNITED STATES PATENT AND TRADEMARK OFFICE
CERTIFICATE OF CORRECTION

PATENT NO.   : 4,693,311
DATED        : September 15, 1987
INVENTOR(S)  : Herman M. Muijs and Paulus P.M. Keijzer It is certified that error appears in the above-identified patent and that said Letters Patent is hereby corrected as shown below:

Claim 1, column 8, line 54, "light" should be --least--.

Claim 6, column 9, line 2, "steam-forming" should be --steam-foam-forming--.

Signed and Sealed this

Thirtieth Day of May, 1989

Attest:

DONALD J. QUIGG

*Attesting Officer*    *Commissioner of Patents and Trademarks*